(12) United States Patent
De Boer

(10) Patent No.: US 11,737,716 B2
(45) Date of Patent: Aug. 29, 2023

(54) KINEMATICAL JOINTS FOR X-RAY SYSTEMS

(71) Applicant: KONINKLIJKE PHILIPS N.V., Eindhoven (NL)

(72) Inventor: Jacob De Boer, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

(21) Appl. No.: 16/649,730

(22) PCT Filed: Sep. 26, 2018

(86) PCT No.: PCT/EP2018/076198
§ 371 (c)(1),
(2) Date: Mar. 23, 2020

(87) PCT Pub. No.: WO2019/063657
PCT Pub. Date: Apr. 4, 2019

(65) Prior Publication Data
US 2020/0237328 A1     Jul. 30, 2020

(30) Foreign Application Priority Data

Sep. 29, 2017  (EP) .................................... 17194024

(51) Int. Cl.
*A61B 6/00* (2006.01)
(52) U.S. Cl.
CPC .......... *A61B 6/4458* (2013.01); *A61B 6/4405* (2013.01); *A61B 6/4441* (2013.01); *A61B 6/4464* (2013.01); *A61B 6/4476* (2013.01)
(58) Field of Classification Search
CPC ... A61B 6/4405; A61B 6/4429; A61B 6/4435; A61B 6/4441; A61B 6/4458; A61B 6/4464; A61B 6/4476; A61B 6/4482
See application file for complete search history.

(56) References Cited

U.S. PATENT DOCUMENTS

| 3,892,967 A | 7/1975 | Grady et al. |
| 4,756,016 A | 7/1988 | Grady et al. |

(Continued)

FOREIGN PATENT DOCUMENTS

| DE | 102014206301 A1 | 3/2015 |
| EP | 0323327 A1 | 7/1989 |
| FR | 2645007 A1 | 10/1990 |

OTHER PUBLICATIONS

PCT/EP2018/076198 WO & ISR, dated Dec. 13, 2018M 13 Page Document.

*Primary Examiner* — Dani Fox
*Assistant Examiner* — Soorena Kefayati

(57) ABSTRACT

A support arrangement for generating an X-ray image is provided. The arrangement includes a support structure configured to hold an image detector at a first end and an X-ray source at a second end, with a connection line in between on which an Iso-centre is located. The support structure connects to a primary supporting beam in a first pivotable connection point; the primary supporting beam connects to a secondary supporting beam in a second pivotable connection point; and the secondary supporting beam connects to a mounting arrangement in a third pivotable connection point. A rhombus shape is defined by: (i) a connection line between the first and second pivotable connection points; (ii) a connection line between the second and third pivotable connection points; (iii) a connection line between the third pivotable connection point and the Iso-centre; and (iv) a connection line between the Iso-centre and the first pivotable connection point.

16 Claims, 4 Drawing Sheets

(56) References Cited

U.S. PATENT DOCUMENTS

| | | | |
|---|---|---|---|
| 4,761,805 A | 8/1988 | Sebring | |
| 4,964,151 A * | 10/1990 | Trotel | F16M 11/2092 378/197 |
| 6,200,024 B1 * | 3/2001 | Negrelli | A61B 6/4476 378/197 |
| 6,213,638 B1 * | 4/2001 | Rattner | A61B 6/467 378/198 |
| 6,461,039 B1 * | 10/2002 | Klotz | A61B 6/4441 378/197 |
| 10,820,871 B1 * | 11/2020 | Martinez Ferreira | A61B 6/4405 |
| 2001/0005410 A1 * | 6/2001 | Rasche | A61B 6/4458 378/197 |
| 2008/0075225 A1 * | 3/2008 | Kalender | A61B 6/4458 378/20 |
| 2008/0167545 A1 * | 7/2008 | Meissner | A61B 8/06 600/407 |
| 2008/0198963 A1 * | 8/2008 | Spahn | A61B 6/4233 378/5 |
| 2008/0247506 A1 * | 10/2008 | Maschke | A61B 6/4476 378/15 |
| 2009/0147924 A1 * | 6/2009 | Gross | A61B 6/56 378/194 |
| 2009/0175421 A1 * | 7/2009 | Gross | A61B 6/4441 378/197 |
| 2009/0271035 A1 * | 10/2009 | Lurz | B25J 9/1664 700/245 |
| 2010/0114308 A1 * | 5/2010 | Maschke | A61B 6/12 623/2.37 |
| 2011/0075798 A1 * | 3/2011 | Boese | A61B 6/4441 378/20 |
| 2011/0075814 A1 * | 3/2011 | Boese | A61B 6/4441 378/197 |
| 2011/0274247 A1 * | 11/2011 | Maschke | A61B 6/4441 378/62 |
| 2011/0280379 A1 * | 11/2011 | Maschke | A61B 6/4458 901/15 |
| 2012/0029694 A1 * | 2/2012 | Muller | A61B 34/37 700/248 |
| 2012/0035470 A1 * | 2/2012 | Kuduvalli | A61B 6/00 600/427 |
| 2013/0083894 A1 * | 4/2013 | Niebler | A61B 6/547 378/62 |
| 2013/0121459 A1 * | 5/2013 | Meyer | A61B 6/4441 378/9 |
| 2014/0163736 A1 * | 6/2014 | Azizian | B25J 9/1676 700/259 |
| 2014/0321612 A1 * | 10/2014 | Schafer | A61B 6/022 378/41 |
| 2015/0093180 A1 * | 4/2015 | Graumann | A61B 6/547 403/14 |
| 2015/0150525 A1 * | 6/2015 | Navab | A61B 6/4441 378/19 |
| 2015/0157283 A1 | 6/2015 | Yamashita | |
| 2016/0193731 A1 * | 7/2016 | Sattler | A61B 34/30 901/9 |
| 2017/0100083 A1 * | 4/2017 | Bauer | A61B 6/5205 |
| 2017/0238897 A1 * | 8/2017 | Siewerdsen | A61B 6/466 |
| 2018/0310904 A1 * | 11/2018 | Kraemer | A61B 6/4441 |
| 2018/0333116 A1 * | 11/2018 | Atzinger | B25J 18/005 |

* cited by examiner

KINEMATICAL JOINTS FOR X-RAY SYSTEMS

CROSS-REFERENCE TO PRIOR APPLICATIONS

This application is the U.S. National Phase application under 35 U.S.C. § 371 of International Application No. PCT/EP2018/076198, filed on Sep. 26, 2018, which claims the benefit of or European Patent Application No. 17194024.0, filed on Sep. 29, 2017. These applications are hereby incorporated by reference herein.

FIELD OF THE INVENTION

The present invention relates to generating X-ray images, and relates, in particular, to an imaging support arrangement for generating an X-ray image, an X-ray imaging system for generating X-ray images and a method for generating X-ray images.

BACKGROUND OF THE INVENTION

To suspend an X-ray source and a detector of an X-ray system, C-arc shaped structures may be used. As an example, a C-arc is used to realize a rotational movement, in particular, an orbital or angulation rotation of the imaging devices, i.e. detector and source, around an object to be irradiated. The rotation may be required during an intervention to acquire e.g. 2D images from different projection directions, or also to provide a plurality of image slices for a 3D reconstruction from multiple images. However, C-arcs may be relatively bulky, for instance when not in use, or they can be relatively heavy, requiring accordingly motorized movement support. Furthermore, rotation range may be limited due to size and complexity of the supporting arrangement. As an example, DE 10 2014 206301 A1 shows a C-arc holding arrangement. However, it has been shown that the operation, especially the control may be cumbersome and a synchronization of all components for an angulation rotation may require some effort. A further example of an X-ray system permitting isocentric movements is shown in U.S. Pat. No. 4,964,151.

SUMMARY OF THE INVENTION

There may thus be a need to provide an improved and facilitated construction for an interventional X-ray system allowing rotation of an imaging arrangement around an object of interest.

The object of the present invention is solved by the subject-matter of the independent claims; further embodiments are incorporated in the dependent claims.

According to the invention, an imaging support arrangement for generating an X-ray image is provided. The imaging support arrangement for generating an X-ray image comprises a support structure, a primary supporting beam, a secondary supporting beam and a mounting arrangement. The support structure is configured to hold an image detector at a first end, and an X-ray source at a second end, with a connection line in between, on which an Iso-centre D can be located. The support structure is connected to the primary supporting beam in a first pivotable connection point A with a first connector, and the primary supporting beam is connected to the secondary supporting beam in a second pivotable connection point B with a second connector, and the secondary supporting beam is connected to the mounting arrangement in a third pivotable connection point C with a third connector.

The first, second and third pivotable connection points (A,B,C) and the Iso-centre D define a rhombus shape. That is, a connection line between the first pivotable connection point A and the second pivotable connection point B, a connection line between the second pivotable connection point B and the third pivotable connection point C, a connection line between the third pivotable connection point C and the Iso-centre D, and a connection line between the Iso-centre D and the first pivotable connection point A form the sides or edges of a rhombus.

As a result, the movement and thus the operation is facilitated and improved.

In an example, the connection points are arranged at an end portion of the beams. In particular, the first and second connection points may be arranged at respective end portions of the first supporting beam, and the second and third connection points may be arranged at respective end portions of the second supporting beam.

According to an example, an angulation rotation movement of the support structure around an Iso-centre D is realized. In particular, the support structure, the primary supporting beam, the secondary supporting beam, the mounting arrangement, and a connection line between the mounting arrangement and the Iso-centre D are coupled in a way that the connection lines, i.e. the first, second, and third pivotable connection points (A), (B), (C) and the Iso-centre (D) remain in a rhombus shape during a movement of the imaging support arrangement around the Iso-centre D in an Iso-centred angulation rotation. The Iso-centre remains in its initial position.

In an example, also the third pivotable connection point remains in its initial position.

In an example, the lines joining the initial and final points of each of the points A, B, C and D of the imaging support arrangement are a set of parallel straight lines, so that the orientation of the imaging support arrangement is moving around the Iso-centre D.

At both ends A and C additional/extra rotation functions can be added to create additional rotations. With additional rotation functions, movements around the area of interest can be further optimized.

At position C, the additional rotation can be added able to position the complete image chain horizontal.

In an example, a sensor arrangement provides a movements-position-tracking and/or accurate positioning and/or memorizing of previous position holds.

In an example, the primary supporting beam and the secondary supporting beam have the same length.

In an example, the primary and secondary supporting beam form or define a "½ rhombus".

In an example, at point C a motor actuation can be applied. Therefore, between A and B a transmission will be applied.

According to an example, at least one of the first, second and third connectors comprises a transmission mechanism. The support structure, the primary supporting beam and the secondary supporting beam are mechanically coupled in a rotational manner around their pivoting points.

In other words, the at least one of the couplings comprise a transmission mechanism In an option, the transmission mechanism comprises transmission units of the group of a belt, toothed belt, chains with chain wheels or cables with pulleys.

In an example, the angulation rotation can be easily motor assisted to increase the ease of use and is therefore also able to realize repeatable positioning and smooth positioning.

In an example, the support structure is attached in the first pivotable point A, such that it is rotatable around the connection line between the first pivotable point A and the Iso-centre D.

According to the invention, also an X-ray imaging system for generating X-ray images is provided. The system comprises an imaging support arrangement. The support structure comprises a detector and an X-ray source. The detector and the X-ray source are mounted to opposing ends of the support structure such that the detector and the X-ray source are rotatably movable around the Iso-centre (D). The imaging support arrangement comprises a support structure, a primary supporting beam, a secondary supporting beam and a mounting arrangement. The support structure is connected to the primary supporting beam in a first pivotable connection point A, and the primary supporting beam is connected to the secondary supporting beam in a second pivotable connection point B. The secondary supporting beam is connected to the mounting arrangement in a third pivotable connection point C and the support structure is rotatable around an Iso-centre D.

In an example, an optimal storage position of the image chain assembly can be realized for fixed and mobile systems during use and storage to create maximum free space and minimum volume claim.

According to an example, the mounting arrangement is attached to a mobile base.

According to an example, the mounting arrangement is attached to a fixed base.

In an example, the mounting arrangement is attached to a ceiling. The mounting arrangement can also be attached to a floor or wall structure.

According to an example, the third connector is movably supported along a circular path at the mounting arrangement.

In an example, the circular path has a virtual center aligned with the Iso-centre.

The movement is provided to translate the pivotable connection point (C) along the circular path, e.g. to extend the angulation range further.

According to an example, the mounting arrangement is attached to an additional C-shape suspension.

The C-shape suspension allows that the angulation range can be extended towards 360°.

According to the invention, also a method for generating X-ray images is provided. The method comprises the following steps:

a) In a first step, an object to be irradiated is arranged in an Iso-centre D of an imaging system comprising an imaging support arrangement with a detector and an X-ray source. The support structure is rotatable around the Iso-centre D and the imaging support arrangement comprises a support structure, a primary supporting beam, a secondary supporting beam and a mounting arrangement.

The support structure is connected to the primary supporting beam in a first pivotable connection point A, and the primary supporting beam is connected to the secondary supporting beam in a second pivotable connection point B.

The secondary supporting beam is connected to the mounting arrangement in a third pivotable connection point C.

b) In a second step, the imaging support arrangement moves around the Iso-centre D in an Iso-centred angulation rotation wherein the support structure, the primary supporting beam, the secondary supporting beam, the mounting arrangement and the connection line between the mounting arrangement and the Iso-centre are coupled in a way that a remaining of the connection lines in a parallelogram shape and a remaining of the Iso-centre and the third pivotable connection point in their initial positions is ensured.

c) In a third step, the X-ray images of the object to be irradiated are generated at different positions along the movement path.

According to an example, the method, in step b), the moving comprises a moving of the pivoting point C along a circular path The angulation range can thus be extended further.

According to an aspect, the invention provides an improved construction for interventional X-ray imaging systems. As an advantage, a simplified control of the angulation rotation around an Iso-centre is provided. The beams are coupled in a way that the detector and the receptor are guided in a parallelogram guidance around the object to be irradiated. A transmission mechanism in the image chain provides an easy transmission. Hence, the synchronisation is provided and the effort for ensuring the correct angular of all components during operation is reduced. The operation is thus facilitated.

The coupled rotational movements of the arms replace the physical connection between the Iso-centre and the coupling to a base.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
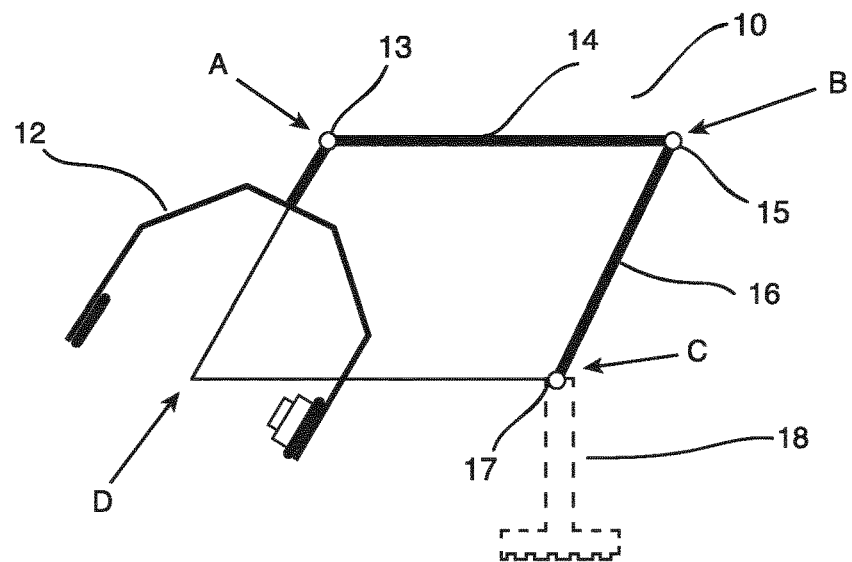
FIG. 1 shows an imaging support arrangement for generating an X-ray image.

FIG. 1 shows an imaging support arrangement 10 for generating an X-ray image. The imaging support arrangement 10 for generating an X-ray image comprises a support structure 12, a primary supporting beam 14, a secondary supporting beam 16, a mounting arrangement 18, wherein the support structure 14 is configured to hold an image detector 22 at a first end and an X-ray source 24 at a second end with a connection line in between, on which an Iso-centre D can be located. The support structure 12 is connected to the primary supporting beam 14 in a first pivotable connection point A with a first connector 13, and the primary supporting beam 14 is connected to the secondary supporting beam 16 in a second pivotable connection point B with a second connector 15, and the secondary supporting beam 14 is connected to the mounting arrangement 18 in a third pivotable connection point C with a third connector 17. The first, second and third pivotable connection points (A,B,C) and the Iso-centre D define, i.e. form a rhombus shape.

The detector can also be referred to as receptor.

Figure 2:
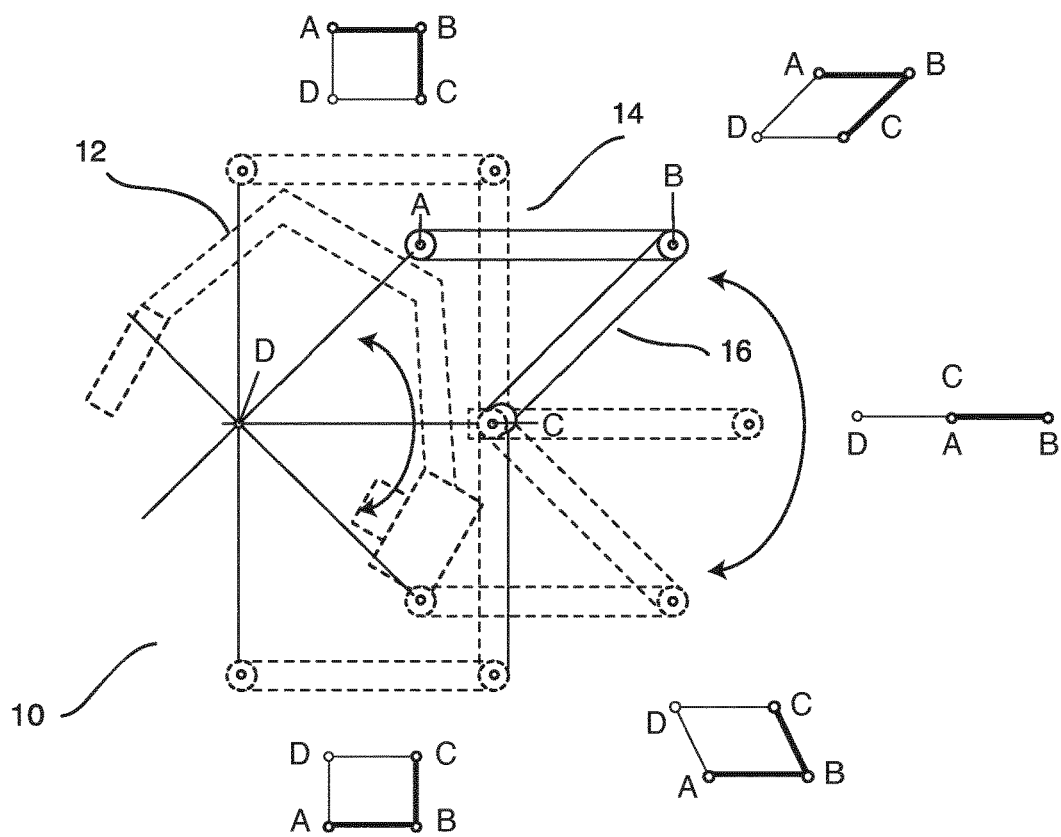
FIG. 2 shows a schematic view of the movement of an imaging support arrangement.

FIG. 2 shows the moving of the imaging support arrangement 10 around an Iso-centre D. The support structure 12 is attached to a primary support beam 14 in a first pivotable connection point A with a first connector 13, the primary support beam 14 is attached to a secondary support beam 16 in second pivotable connection point B with a second connector 15, and the secondary support beam 16 is attached to a mounting arrangement in a third pivotable connection point C with a third connector 17. The virtual parallelogram remains in the parallel shape during the moving around the Iso-centre (D). In an example, not shown, at least one of the couplings in point A, B and C is motor-driven and the support structure, the primary supporting beam and the secondary supporting beam are mechanically coupled in a rotational manner around their pivoting points.

In another example, not shown, at point C also a motor actuation can be applied, with this second motor a vertical height position can be created and also an advantageous storage position or advantageous favourable transport position for mobile surgery systems.

In an example, not shown, the support structure, supporting beams, motors, rotations points, transmissions and brake mechanisms are traditional components.

According to an example, not shown, the first connector 13 is rotatable around a rotation axis defined by the connection line between the first pivotable point (A) and the Iso-centre (D).

In an example, the arrangement comprises 4 rotation points wherein the Iso-centre D can also be referred to as virtual point D.

According to another example, not shown, the cabling needed for the X-ray source and detector and other parts connected with the support structure can be integrated in the imaging support structure, this will improve the clean ability and avoid cabling entangling during movements.

Integrated cabling also avoids rubbing which causes unwanted contamination.

In an example, the imaging support arrangement is a light weighted structure with high stiffness.

In an example, the imaging support arrangement is able to realize a larger than 180° angulation rotation range.

In an example, the outside dimensions and shape of the imaging support arrangement can be optimized since balancing is not required anymore such that a free optimized imaging support structure can be designed and a traditional C-arc structure is not required anymore.

In an example, the support structure is C-shaped.

The system for generating an X-ray image can also be referred to as "image chain assembly" or "image chain".

In every position the connection lines A-B, B-C, C-D and D-A define a parallelogram.

Figure 3A:
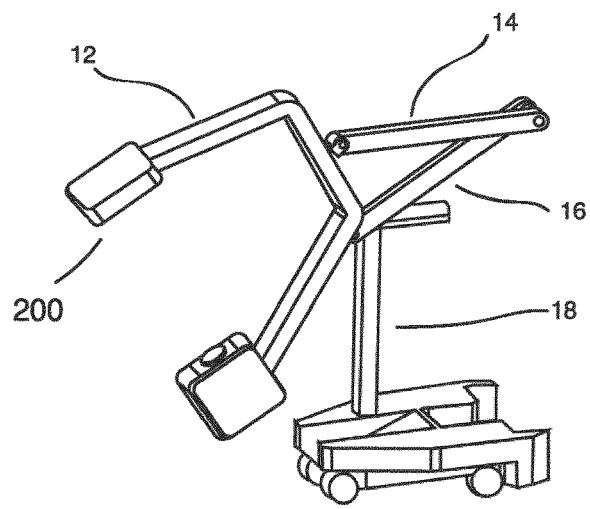
FIG. 3A shows a mounting arrangement attached to a mobile base.

FIG. 3A shows an embodiment with a mounting arrangement attached to mobile base 200.

Figure 3B:
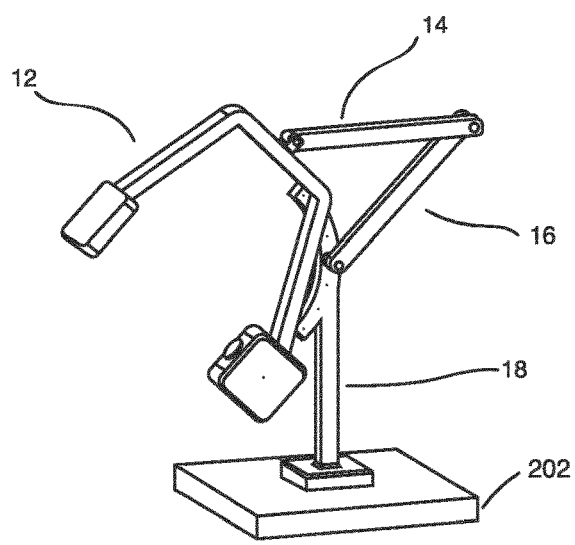
FIG. 3B shows a mounting arrangement attached to a fixed base.

FIG. 3B shows an embodiment with a mounting arrangement attached to a fixed base 202. The fixed base 202 may be attached to a floor (not shown).

Figure 3C:
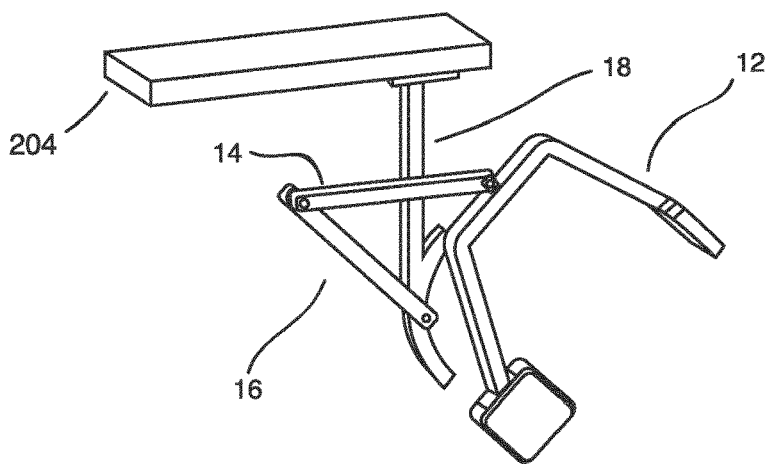
FIG. 3C shows a mounting arrangement attached to a fixed base.

FIG. 3C shows an embodiment with a mounting arrangement attached to a fixed base 204. The fixed base 204 may be attached to a ceiling (not shown).

Figure 4:
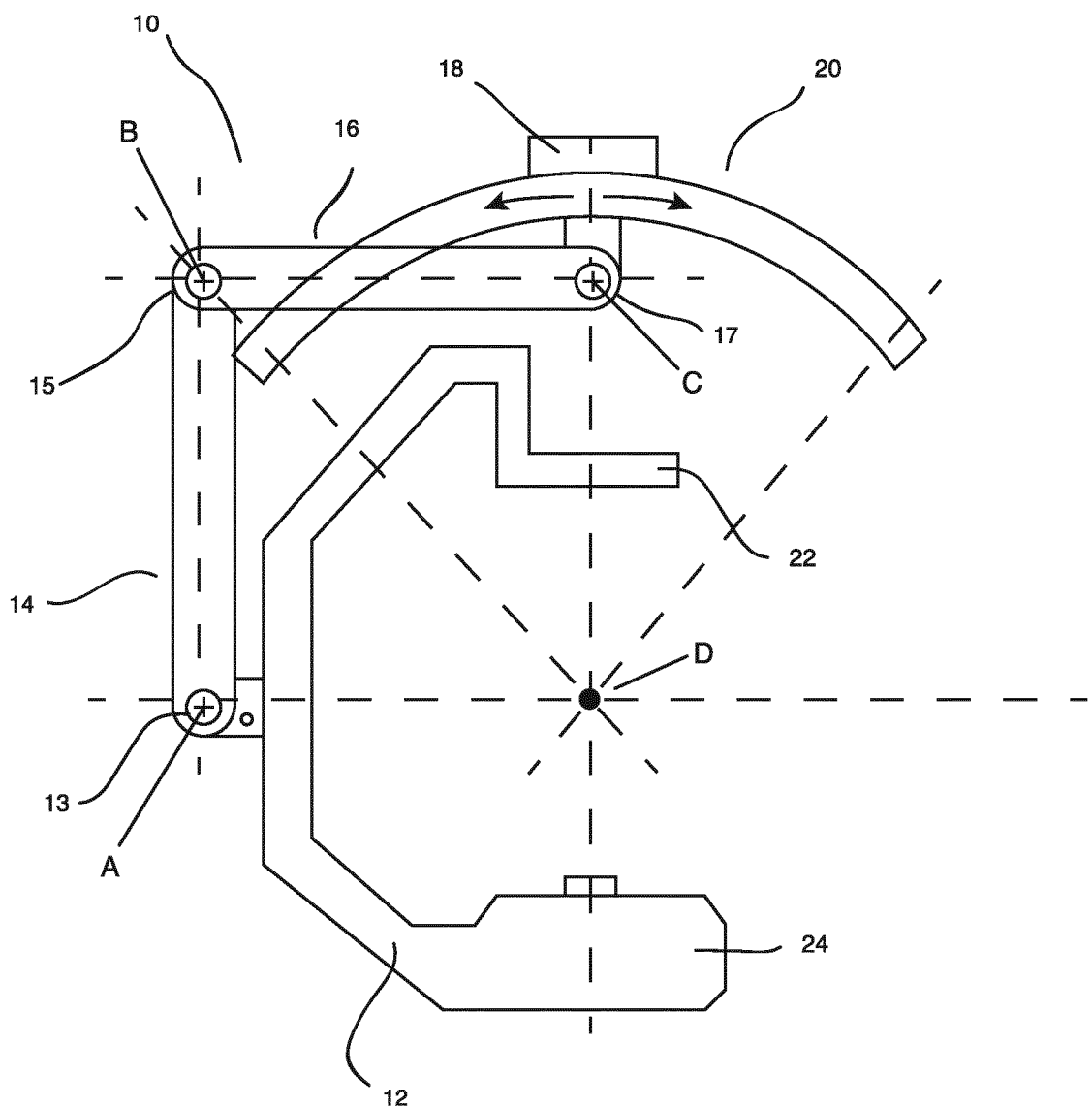
FIG. 4 shows an imaging support arrangement with an additional C-shape suspension.

FIG. 4 shows an imaging support arrangement 10 with an additional C-shape suspension 20. The support structure 12, comprising the detector 22 and the X-ray source 24, is attached to the primary support beam 14 in a first pivotable connection point A with a first connector 13. The primary support beam 14 is attached to a secondary support beam 16 in second pivotable connection point B with a second connector 15, and the secondary support beam 16 is attached to an additional C-shape suspension 20 in a third pivotable connection point C with a third connector. The length of the C-shape can be selected and will define the total angulation/roll range and will further extend the range of the ½ rhombus. With this additional C-shape suspension 20 the angulation range can be extended towards 270° or even 360°.

In an example, not shown, actuating at point C means that point B will be rotated with the same angle rotation when the transmission is 1:1.

In an example, other transmissions are possible.

Figure 5:
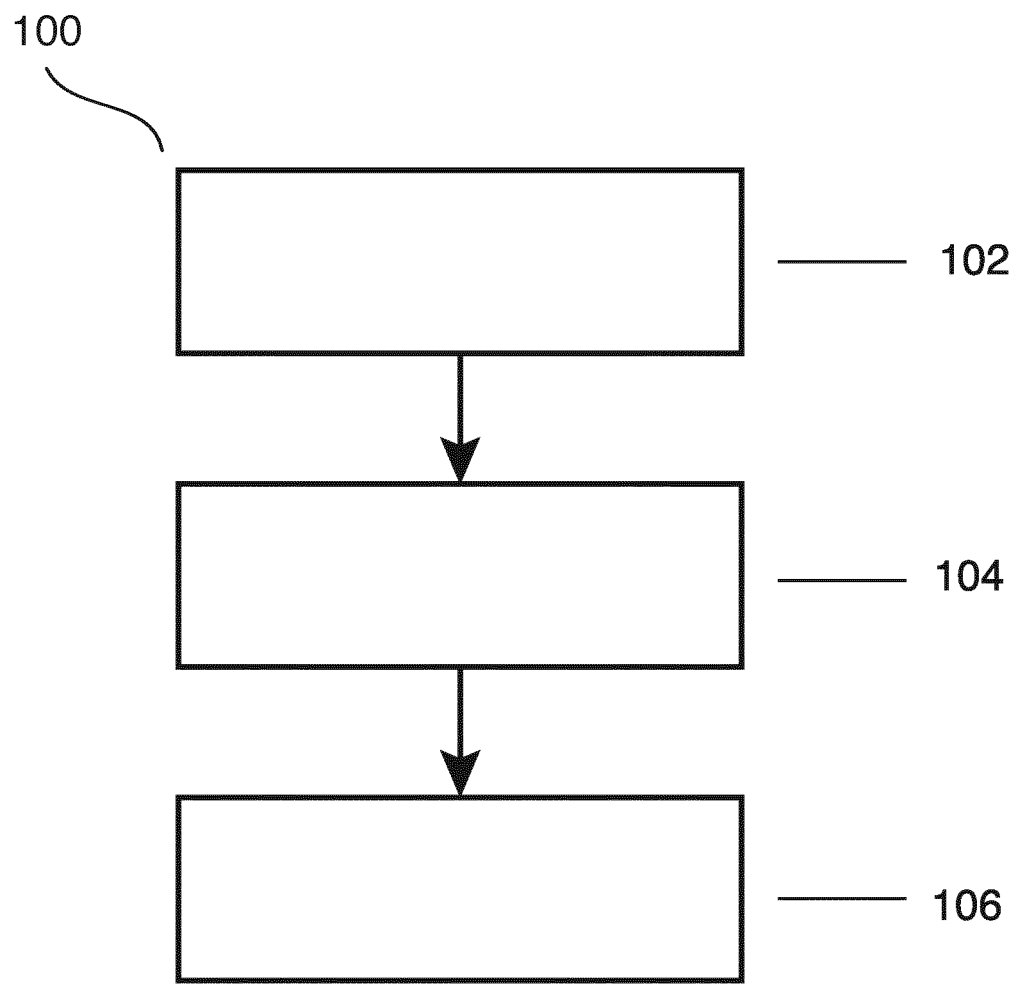
FIG. 5 shows an example of a method for generating X-ray images.

FIG. 5 shows a method 100 for generating X-ray images, comprising the following steps:
a) arranging 102 an object to be irradiated in an Iso-centre D of an imaging system 50
b) moving 104 the imaging support arrangement 10 around the Iso-centre D in an Iso-centred angulation; and
c) generating 106 X-ray images of the object to be irradiated at different positions along a movement path.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single device or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging support arrangement for generating an X-ray image, comprising:
   a support structure configured to hold an image detector at a first end and an X-ray source at a second end, with a connection line in between, wherein the support structure is connected to a primary supporting beam in a first pivotable connection point with a first connector,
   the primary supporting beam connected to a secondary supporting beam in a second pivotable connection point with a second connector,
   the secondary supporting beam connected to a mounting arrangement in a third pivotable connection point with a third connector,
   wherein the support structure, the primary supporting beam, the secondary supporting beam, and the mounting arrangement are mechanically coupled in a rotational manner around the first pivotable connection point, the second pivotable connection point, and third pivotable connection point such that a rhombus shape is defined by connection lines comprising:
   i) a connection line between the first pivotable connection point and the second pivotable connection point,
   ii) a connection line between the second pivotable connection point and the third pivotable connection point,
   iii) a connection line between the third pivotable connection point and an Iso-centre located on the connection line in between the first end and the second end of the support structure, and
   iv) a connection line between the Iso-centre and the first pivotable connection point,
   wherein the connection lines remain in the rhombus shape during a movement of the imaging support arrangement around the Iso-centre in an Iso-centred angulation rotation, and
   wherein the third connector is movably supported by an additional C-shape suspension.

2. The imaging support arrangement according to claim 1, wherein during the movement of the imaging support arrangement around the Iso-centre in the Iso-centred angulation rotation, the Iso-centre remains in an initial position.

3. The imaging support arrangement according to claim 1, wherein at least one of the first connector, the second connector, and the third connector comprises a transmission mechanism.

4. The imaging support arrangement according to claim 1, wherein the first connector is rotatable around a rotation axis defined by the connection line between the first pivotable connection point and the Iso-centre.

5. An X-ray imaging system for generating X-ray images, comprising:
   the imaging support arrangement according to claim 1; and
   an imaging arrangement comprising the image detector and the X-ray source,
   wherein the image detector and the X-ray source are mounted to opposing ends of the support structure such that the image detector and the X-ray source are rotatably movable around the Iso-centre.

6. The imaging support arrangement according to claim 1, further comprising a sensor arrangement configured to provide movements-position-tracking of positions of the imaging support arrangement.

7. The imaging support arrangement according to claim 1, wherein at least one of the first connector, the second connector, and the third connector is motor-driven.

8. The X-ray imaging system according to claim 5, wherein the mounting arrangement is attached to a mobile base.

9. The X-ray imaging system according to claim 5, wherein the mounting arrangement is attached to a fixed base.

10. The X-ray imaging system according to claim 5, wherein the third connector is movably supported along a circular path at the mounting arrangement.

11. A method for generating X-ray images, comprising:
    arranging an object to be irradiated in the Iso-centre of the X-ray imaging system according to claim 5;
    moving the imaging support arrangement around the Iso-centre in the Iso-centred angulation rotation; and
    generating X-ray images of the object to be irradiated at different positions along a movement path.

12. The method according to claim 11, wherein the moving comprises a moving of the third pivotable connection point along a circular path.

13. The method according to claim 11, further comprising providing movements-position-tracking of positions of the imaging support arrangement.

14. A non-transitory computer-readable storage medium having stored a computer program comprising instructions for controlling an X-ray imaging system for generating X-ray images, the instructions, when the computer program is executed by a computer, cause the computer to:
    control movement of an imaging support arrangement of the X-ray imaging system around an Iso-centre in an Iso-centred angulation rotation to irradiate an object for generating an X-ray image, the imaging support arrangement comprising:

a support structure i-s-configured to hold an image detector at a first end and an X-ray source at a second end with a connection line in between, the support structure is connected to a primary supporting beam in a first pivotable connection point with a first connector, the primary supporting beam is connected to a secondary supporting beam in a second pivotable connection point with a second connector, and the secondary supporting beam is connected to a mounting arrangement in a third pivotable connection point with a third connector, wherein the support structure, the primary supporting beam, the secondary supporting beam, and the mounting arrangement are mechanically coupled in a rotational manner around the first pivotable connection point, the second pivotable connection point, and third pivotable connection point such that a rhombus shape is defined by connection lines comprising:

i) a connection line between the first pivotable connection point and the second pivotable connection point, ii) a connection line between the second pivotable connection point and the third pivotable connection point, iii) a connection line between the third pivotable connection point and the Iso-centre located on the connection line in between the first end and the second end of the support structure, and iv) a connection line between the Iso-centre and the first pivotable connection point; and an imaging arrangement comprising the image detector and the X-ray source, wherein the third connector is movably supported by an additional C-shape suspension;

wherein the coupling of the support structure, the primary supporting beam, the secondary supporting beam, and the mounting arrangement is configured so that the connection lines remain in the rhombus shape during the movement of the imaging support arrangement around the Iso-centre in the Iso-centred angulation rotation; and generate the X-ray images of the irradiated object to be irradiated at different positions along a movement path.

15. The non-transitory computer-readable storage medium of claim 14, wherein the instructions, when the computer program is executed by the computer, further cause the computer to provide movements-position-tracking of positions of the imaging support arrangement.

16. The non-transitory computer-readable storage medium of claim 14, wherein at least one of the first connector, the second connector, and the third connector is motor-driven.

* * * * *